United States Patent
Takenaka et al.

(10) Patent No.: US 9,815,855 B2
(45) Date of Patent: Nov. 14, 2017

(54) METHOD FOR PRODUCING 4-BORONO-L-PHENYLALANINE HAVING 18F ATOM INTRODUCED THEREINTO, AND PRECURSOR OF 4-BORONO-L-PHENYLALANINE HAVING 18F ATOM INTRODUCED THEREINTO

(71) Applicants: STELLA PHARMA CORPORATION, Osaka (JP); OSAKA PREFECTURE UNIVERSITY PUBLIC CORPORATION, Osaka (JP)

(72) Inventors: Hiroshi Takenaka, Osaka (JP); Yoichiro Ohta, Osaka (JP); Yusuke Taguchi, Osaka (JP); Sayuri Ueda, Osaka (JP); Yuko Ishino, Osaka (JP); Tomohiro Yoshikawa, Osaka (JP); Hideki Nakashima, Osaka (JP); Kohki Uehara, Osaka (JP); Mitsunori Kirihata, Osaka (JP)

(73) Assignees: Stella Pharma Corporation, Osaka (JP); Osaka Prefecture University Public Corporation, Osaka (JP)

(*) Notice: Subject to any disclaimer, the term of this patent is extended or adjusted under 35 U.S.C. 154(b) by 0 days.

(21) Appl. No.: 15/122,118

(22) PCT Filed: Jan. 28, 2015

(86) PCT No.: PCT/JP2015/052303
§ 371 (c)(1),
(2) Date: Aug. 26, 2016

(87) PCT Pub. No.: WO2015/129374
PCT Pub. Date: Sep. 3, 2015

(65) Prior Publication Data
US 2017/0015684 A1    Jan. 19, 2017

(30) Foreign Application Priority Data

Feb. 28, 2014    (JP) .................................. 2014-038001

(51) Int. Cl.
C07F 5/02        (2006.01)
C07C 45/63       (2006.01)
(Continued)

(52) U.S. Cl.
CPC .............. *C07F 5/025* (2013.01); *C07B 59/00* (2013.01); *C07B 59/004* (2013.01); *C07C 45/63* (2013.01); *C07C 47/55* (2013.01); *C07B 2200/05* (2013.01)

(58) Field of Classification Search
None
See application file for complete search history.

(56) References Cited

U.S. PATENT DOCUMENTS

2015/0329564 A1* 11/2015 Takenaka .................. C07F 5/04
558/298

FOREIGN PATENT DOCUMENTS

CN        102887913 A       1/2013
WO    WO 2016065145    *    4/2016

OTHER PUBLICATIONS

Forngren ("Synthesis of [4-18F]-1-Bromo-4-fluorobenzene and its Use in Palladium-Promoted Cross-Coupling Reactions with Organostannanes" Acta Chemica Scandinavica, 1998, 52, p. 475-479).*

(Continued)

*Primary Examiner* — Jafar Parsa
*Assistant Examiner* — Amy C Bonaparte
(74) *Attorney, Agent, or Firm* — Knobbe, Martens, Olson & Bear, LLP

(57) ABSTRACT $^{18}$F-labeled 4-boronophenylalanine (BPA) can be produced by preparing and further processing a precursor of $^{18}$F-labeled BPA represented by the following formula:

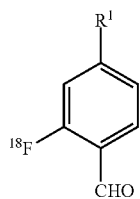

in which $R^1$ represents a bromo group, an iodo group, a fluoro group, a diazaborinane derivative, $BX_3^-$ or $BX_3^-M^+$ (wherein X represents a halogen atom; and $M^+$ represents a monovalent monoatomic cation, a polyatomic cation or a complex cation).

4 Claims, 2 Drawing Sheets

(51) Int. Cl.
*C07B 59/00* (2006.01)
*C07C 47/55* (2006.01)

(56) References Cited

OTHER PUBLICATIONS

Allain-Barbier ("Synthesis of [4-18F]fluorophenyl-alkene and -arenes via Palladium-Catalyzed Coupling of 4-[18F]Fluoroiodobenzene with Vinyl and Aryl Tin Reagents" Acta Chemica Scandinavica, 1998, 52, p. 480-489).*

Yang ("[18F]Fluorobenzoyllysinepentanedioic Acid Carbamates: New Scaffolds for Positron Emission Tomography (PET) Imaging of Prostate-Specific Membrane Antigen (PSMA)" J. Med. Chem. 2016, 59, p. 206-218).*

Jyrki K. Vahatalo, et al., "Synthesis of 4-dihydroxyboryl-2-[ 18F] fluorophenylalanine with relatively high-specific activity," Journal of Labelled Compounds and Radiopharmaceuticals, 2002, vol. 45, 697-704.

Kiichi Ishikawa, et al., "Synthesis and Radiation Dosimetry of 4-Borono-2-[18P]fluoro-D,L-phenylalanine: a Target Compound for PET and Boron Neutron Capture Therapy," Applied Radiation and Isotopes, 1991, vol. 42, No. 4, 325-328.

M. J. Al-Darwich, et al., Enantioselective syntheses of no-carrier -added (n.c .a.) (S) -4-chloro-2- [18p]fluorophenylalanine and (S)-( a-methyl)-4-chloro-2-[18p] fluorophenylalanine and (s)-(a-methy)-4-chloro-2-[18p]fluorophenylalanine, Journal of Flourine Chemistry, 1996, vol. 80, 117-124.

Resarch representative Hiroshi Fukuda, "Development of positron emitter labeled agents for boron neutron capture therapy", Kagaku Kenkyuhi Josei Jigyo (Gakujutsu Kenkyu Josei Kikin Joseikin) Kenkyu Seika Hokokusho, Mar. 3, 2015 (Mar. 3, 2015).

International Search Report dated Mar. 24, 2015 for International Application No. PCT/JP2015/052303.

English translation of Written Opinion mailed by Japan Patent Office dated Mar. 24, 2015 in the corresponding PCT Application No. PCT/JP2015/052303—6 pages.

Extended European Search Report received in European Patent Application No. 15754420.6, dated Jun. 28, 2017.

\* cited by examiner

METHOD FOR PRODUCING 4-BORONO-L-PHENYLALANINE HAVING 18F ATOM INTRODUCED THEREINTO, AND PRECURSOR OF 4-BORONO-L-PHENYLALANINE HAVING 18F ATOM INTRODUCED THEREINTO

INCORPORATION BY REFERENCE TO ANY PRIORITY APPLICATIONS

This application is the U.S. National Phase of International Application No. PCT/JP2015/052303, filed Jan. 28, 2015, designating the U.S. and claiming priority to Japanese Application No. 2014-038001, filed Feb. 28, 2014. Any and all applications for which a foreign or domestic priority claim is identified here or in the Application Data Sheet as filed with the present application are hereby incorporated by reference under 37 CFR 1.57.

FIELD OF THE INVENTION

The present invention relates to a method for producing 4-borono-L-phenylalanine having 18F atom introduced thereinto (fluorinated BPA) (BPA:4-Boronophenylalanine), and precursors thereof.

BACKGROUND OF THE INVENTION

At present, attention has been paid to positron emission tomography (PET) as a technique that is high in sensitivity to be excellent in quantitatively determining performance and can form images easily in light of a principle thereof. This technique has widely been used. The half value period of PET diagnostic reagents (tracers) used for diagnoses is short, and the tracers are each administrated in a fine amount so that any living body is hardly exposed to radiation based thereon. Therefore, this inspecting method is a low invasive inspecting method, thus is greatly advantageous to PET. Furthermore, PET is highly sensitive even to tumors that are not easily determined by CT (computed tomography) or MRI (magnetic resonance imaging), and tumor tissues thereof can be evaluated according to images.

18F-labeled BPA, in which a 18F-fluorine atom is introduced into BPA, which is a boronated amino acid used as a boron reagent for BNCT (boron neutron capture therapy), was developed as a molecular probe for PET by Ishiwata in 1991 (Non-Patent Document 1). Thereafter, a PET inspection with the use of 18F-labeled BPA using the present probe has been an important technique for supporting BNCT. In other words, in clinical and research spots, a 18F-BPA PET image obtained by measuring a subject beforehand can give data on an internal accumulation distribution of BPA, the ratio of tumor tissues/normal tissues (the T/N ratio) and others. On the basis of these data, curative effects of BNCT can be beforehand assumed and then a research or therapeutic plan can be drawn up.

In Ishiwata's synthesis method, BPA is directly fluorinated to prepare 18F-labeled BPA, and 18F+ is used as an electrophilic reagent. From deuterium (D) and neon (Ne) accelerated by a cyclotron, 18F gas is prepared, and then passed through a column filled with sodium acetate to convert the gas to CH3COO-18F+. Thereafter, a solution of BPA in trifluoroacetic acid is bubbled by the introduction of this conversion-obtained compound into the solution. In this way, the synthesis of the target 18F-labeled BPA is attained.

As another method for synthesizing 18F-labeled BPA, Vahatalo et al. suggest a method in which such a conventional method is partially improved (Non-Paten Document 2). This method is a method of using $H^{18}F$, which can be obtained in a larger quantity, to attain the synthesis via $CH3^{18}F$ as an intermediate of $^{18}F_2$. By causing $CH_3I$ to react with $H^{18}F$, which is obtained through the radiation of protons to $H_2^{18}O$ [through $^{18}O(p, n)^{18}F$ reaction], $CH_3^{18}F$ is once synthesized. The resultant compound $CH_3^{18}F$ is discharged to disassociate its C—F bonds to prepare $^{18}F_2$. This compound is used to synthesize $^{18}F$-labeled BPA, equivalently to Ishiwata's synthesis method.

PRIOR ART DOCUMENTS

Non-Patent Documents

Non-Patent Document 1: Appl. Radiat. Isot., 42, 325, 1991

Non-Patent Document 2: J. Label. Compd. Radiopharm., 45, 697, 2002

SUMMARY OF THE INVENTION

Problems to be Solved by the Invention

However, the 18F-labeled BPA obtained by the conventional synthesis method according to Ishiwata et al. is low in specific radioactivity and further extremely small in yield. Even by the improved method, the yield is still small although the specific radioactivity of the resultant $^{18}F$-labeled BPA species is heightened.

One of the objectives of the present invention is to provide a novel BPA derivative that can be an intermediate for synthesizing $^{18}F$-labeled BPA.

Another objective of the present invention is to provide a method for producing such a novel BPA derivative, and a method for producing fluorinated BPA, including $^{18}F$-labeled BPA, using this derivative.

Means for Solving the Problems

In order to solve the above-mentioned problems, the inventors have made eager investigations to find out a novel method for synthesizing BPA. Thus, the present invention has been achieved.

Accordingly, the present invention relates to a compound represented by the following formula:

[Formula 1]

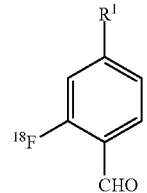

where $R^1$ represents bromo group, iodo group, fluoro group, a diazaborinane derivative, $BX_3^-$, or $BX_3^-M^+$ (X represents halogen, and $M^+$ represents monovalent monoatomic cation, polyatomic cation, or complex cation).

The present invention further relates to a method for producing a compound below:

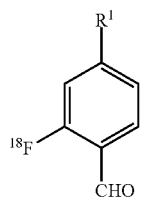

[Formula 3]

where R¹ represents bromo group, iodo group, fluoro group, a diazaborinane derivative, $BX_3^-$, or $BX_3^-M^+$ (X represents halogen, and $M^+$ represents monovalent monoatomic cation, polyatomic cation, or complex cation), comprising a step of using a compound below:

[Formula 2]

where R¹ represents bromo group, iodo group, fluoro group, a diazaborinane derivative, $BX_3^-$, or $BX_3^-M^+$ (X represents halogen, and $M^+$ represents monovalent monoatomic cation, polyatomic cation, or complex cation), and R² represents any one of halogen, amino group, nitro group, boronic acid or boronic acid ester, $OSO_2R^3$, $NR^4R^5$, and $N^+R^4R^5R^6R^7$ (where R³ represents alkyl group having 1 to 7 carbon atoms, halogen-substituted alkyl group having 1 to 7 carbon atoms, or optionally substituted phenyl group; R⁴ and R⁵, which are the same or different, each represent alkyl group having 1 to 7 carbon atoms, halogen-substituted alkyl group having 1 to 7 carbon atoms, or optionally substituted phenyl group, or else R⁴ and R⁵ are combined together with N to form a 3- to 7-membered cyclic structure; R⁶ represents alkyl group having 1 to 7 carbon atoms; and R⁷ represents halogen or sulfonate).

The present invention further relates to a method for producing ¹⁸F-labeled BPA, comprising a step of using a compound below:

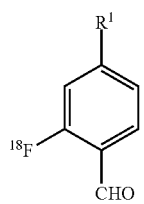

[Formula 4]

where R¹ represents bromo group, iodo group, fluoro group, chloro group, nitro group, amino group, a diazaborinane derivative, $BX_3^-$, or $BX_3^-M^+$ (X represents halogen, and $M^+$ represents monovalent monoatomic cation, polyatomic cation, or complex cation).

In the method for producing ¹⁸F-labeled BPA above, X represents F, and $M^+$ represents an alkali metal ion, an ammonium ion, a tetraalkylammonium ion, a tetraarylammonium ion, a tetraalkylphosphonium ion, a tetraarylphosphonium ion, or an imidazolium ion.

Effect of the Invention

The novel compound and production method of the present invention are favorably usable, particularly, for producing ¹⁸F-labeled BPA.

DETAILED DESCRIPTION OF THE INVENTION

Figure 1:
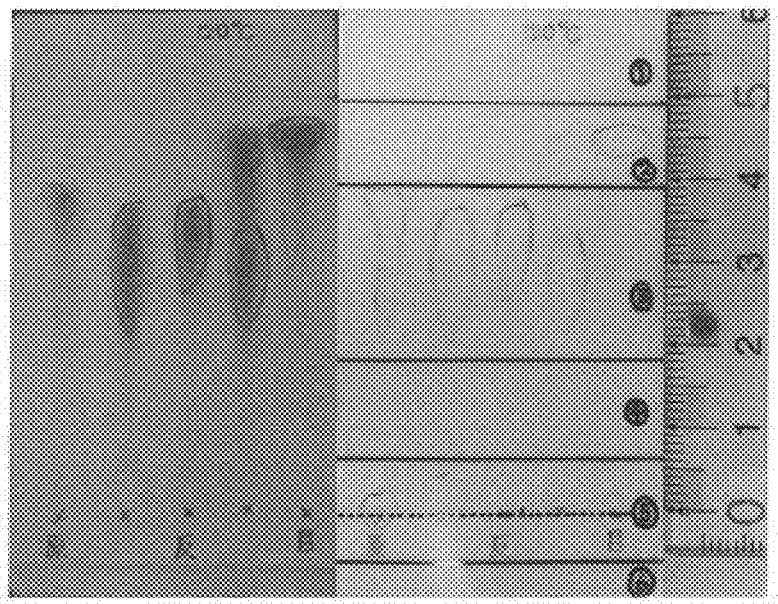
FIG. 1 shows a result of thin layer chromatography that confirms synthesis of a novel compound of the present invention.

The existing methods for synthesizing ¹⁸F-labeled BPA are methods for fluorinating BPA directly, and are attained, in particular, by conducting an electrophilic reaction by use of ¹⁸F as an electrophilic reagent. The inventors have paid attention to the following: in the step of preparing $^{18}F_2$ gas in a cyclotron, the step of using $F^+$ from the resultant $^{18}F_2$ gas, and some other steps in such an existing synthesis route, problems are caused, respectively; and further, ¹⁸F-labeled BPA obtained finally has a lowered specific radioactivity by the generation of a reaction product from intermingled $^{19}F_2$ molecules or by some other causes, and the quantity of ¹⁸F-labeled BPA usable for PET diagnosis according to single synthesis is a quantity for several persons. A novel method of the present invention for synthesizing ¹⁸F-labeled BPA is entirely different from the conventional methods, and is a synthesis method in which ¹⁸F anions are usable. This method makes a load onto the apparatus small, and makes it possible to synthesize ¹⁸F-labeled BPA to give a yield larger than the respective yields according to the conventional synthesis methods.

In the present invention, firstly, a novel method for producing fluorinated BPA, in particular, a method for producing ¹⁸F-labeled BPA, is found out. Further, the present invention provides a novel intermediate compound that can be used in the novel method for producing ¹⁸F-labeled BPA. By this novel method for producing ¹⁸F-labeled BPA, ¹⁸F-labeled BPA can be obtained at a high yield in a simple and convenient manner.

In the present invention, the ¹⁸F-labeled BPA denotes the following.

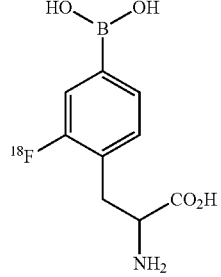

[Formula 5]

The present invention provides a novel intermediate compound that finally lead to synthesis of this $^{18}$F-labeled BPA compound, and a production method.

In the present invention, the novel compound has the same meaning as a compound represented by the following formula:

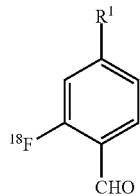

[Formula 6]

where $R^1$ represents bromo group, iodo group, fluoro group, a diazaborinane derivative, $BX_3^-$, or $BX_3^-M^+$ (X represents halogen, and $M^+$ represents monovalent monoatomic cation, polyatomic cation, or complex cation).

The halogen as $R^1$ is particularly preferably bromo group or iodo group, although not limited thereto.

In the present invention, the diazaborinane derivative as $R^1$ is particularly preferably diaminonaphthalene-protected boronic acid, that is, 2,3-dihydro-1H-naphtho[1,8-de][1,3,2]diazaborinine, although not limited thereto. Here, a boron atom is involved in the bond.

In the above $BX_3^-$ or $BX_3^-M^+$, Xs each represent F, and $M^+$ is in particular preferably an alkali metal ion, an ammonium ion, a tetraalkylammonium ion, a tetraarylammonium ion, a tetraalkylphosphonium ion, a tetraarylphosphonium ion, or an imidazolium ion, although not limited thereto.

In the present invention, a method for producing such a novel compound can undergo a step of using the following compound:

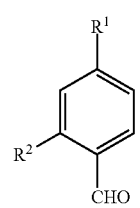

[Formula 7]

where $R^1$ represents bromo group, iodo group, fluoro group, a diazaborinane derivative, $BX_3^-$, or $BX_3^-M^+$ (X represents halogen, and $M^+$ represents monovalent monoatomic cation, polyatomic cation, or complex cation), and $R^2$ represents halogen, amino group, nitro group, boronic acid or boronic acid ester, $OSO_2R^3$, $NR^4R^5$, or $N^+R^4R^5R^6R^7$. Here, $R^3$ represents alkyl group having 1 to 7 carbon atoms, halogen-substituted alkyl group having 1 to 7 carbon atoms, or optionally substituted phenyl group; $R^4$ and $R^5$, which may be the same or different, each represent alkyl group having 1 to 7 carbon atoms, halogen-substituted alkyl group having 1 to 7 carbon atoms, or optionally substituted phenyl group, or else $R^4$ and $R^5$ are combined together with N to form a 3- to 7-membered cyclic structure; $R^6$ represents alkyl group having 1 to 7 carbon atoms; and $R^7$ represents halogen or sulfonate. As the sulfonate, $CF_3SO_3$—, $MeSO_3$—, and TsO— (— indicates the side to be bonded) are particularly preferable.

In the present invention, $^{18}$F-labeled BPA can be produced by using a compound represented by:

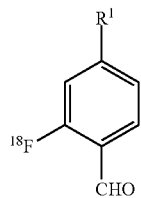

[Formula 8]

where $R^1$ represents halogen, nitro group, amino group, a diazaborinane derivative, $BX_3^-$, or $BX_3^-M^+$ (X represents halogen, and $M^+$ represents monovalent monoatomic cation, polyatomic cation, or complex cation).

In the present invention, the diazaborinane derivative as $R^1$ is particularly preferably 2,3-dihydro-1H-naphtho[1,8-de][1,3,2]diazaborinine, although not limited thereto.

In the present invention, the boronic acid ester as $R^2$ is in particular preferably one selected from the group consisting of selected from the group consisting of pinacol, 2,2-dimethyl-1,3-propanediol, N-methyldiethanolamine, 1,8-diaminonaphthalene, N-methyliminodiacetic acid, 1,1,1-tris-hydroxymethylethane, and catechol, although not limited thereto.

The $^{18}$F-labeled BPA obtained by the production method of the present invention is particularly preferably provided, for example, for preparing PET diagnostic pharmaceuticals, although not limited thereto.

In the present specification, the wording "are combined together with N to form a cyclic structure having 3 to 7 atoms" denotes a saturated or unsaturated ring having carbon and nitrogen. Examples of the ring include, but are not limited to, piperidine, piperazine, pyrrolidine, pyridine, pyrimidine, pyrazine, pyrazole, and imidazole.

In the present invention, the alkyl group having 1 to 7 carbon atoms is in particular preferably a methyl, ethyl, n-propyl, iso-propyl, n-butyl, iso-butyl, sec-butyl, tert-butyl, or n-pentyl group. The halogen-substituted alkyl group denotes an alkyl group having 1 to 7 carbon atoms wherein any number of hydrogen atoms is substituted with one or more halogens. The halogen-substituted alkyl group is preferably a trifluoromethyl group, although the group is not limited. The substituted phenyl group denotes a phenyl group, or a phenyl group having, at one to three positions of the phenyl group, one or more substituents independently of each other. The substituted 3- to 10-membered ring denotes a 3- to 10-membered ring, or a 3- to 10-membered ring having, at one to three positions of the 3- to 10-membered ring, one or more substituents independently of each other. Here, the substituent denotes an alkyl group having 1 to 7 carbon atoms or an alkoxy group having 1 to 7 carbon atoms, although not limited thereto.

Examples of the novel method of the present invention for producing $^{18}$F-labeled BPA include Step α and Step β below using the novel compound of the present invention, although the steps are not limited thereto. Here, the protecting groups used in the following reaction formulae may be appropriately changed, and the protecting groups are not limited to these examples. Further, the novel method of the present invention for producing $^{18}$F-labeled BPA can advance, for example, the reaction of α-1 to α-7 of Step α or β-7 to β-10 of Step β by undergoing the reaction exemplified in Step γ.

Step α
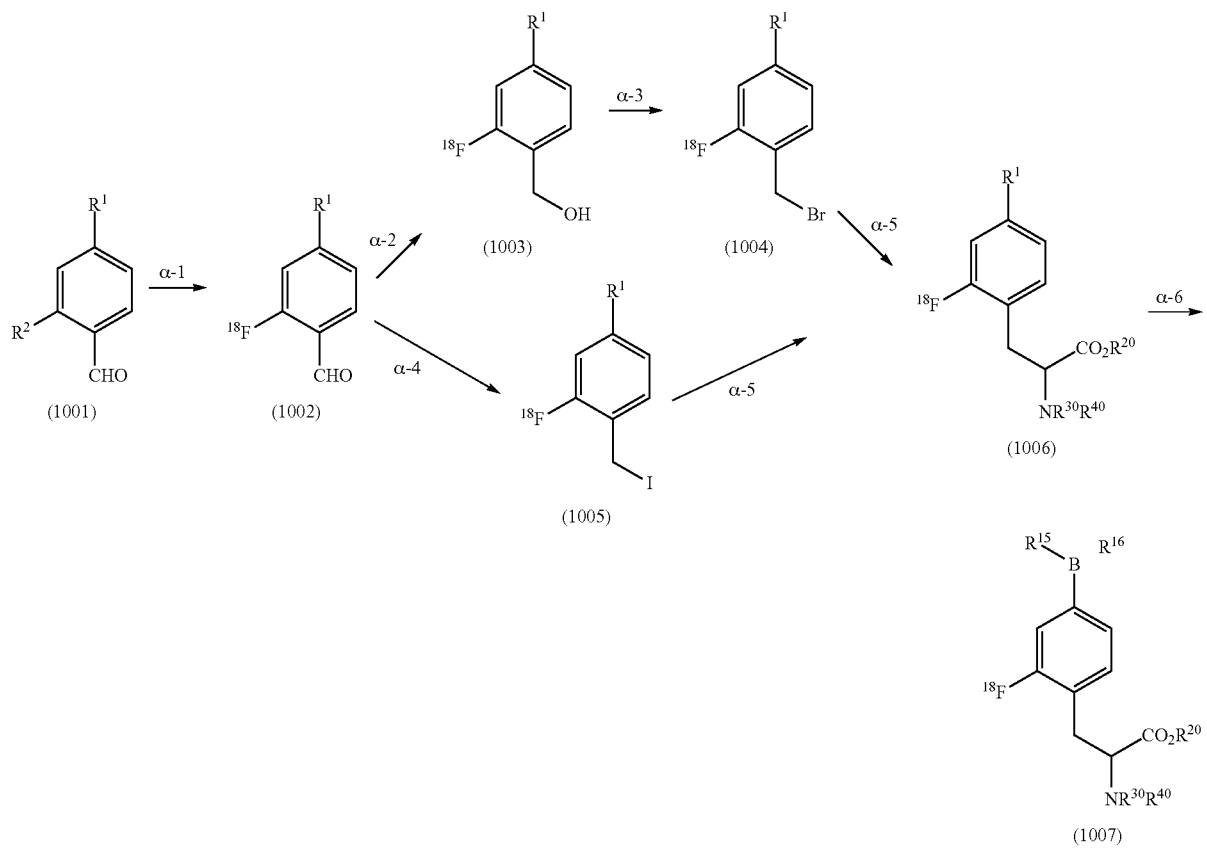
[Formula 9]
Step β
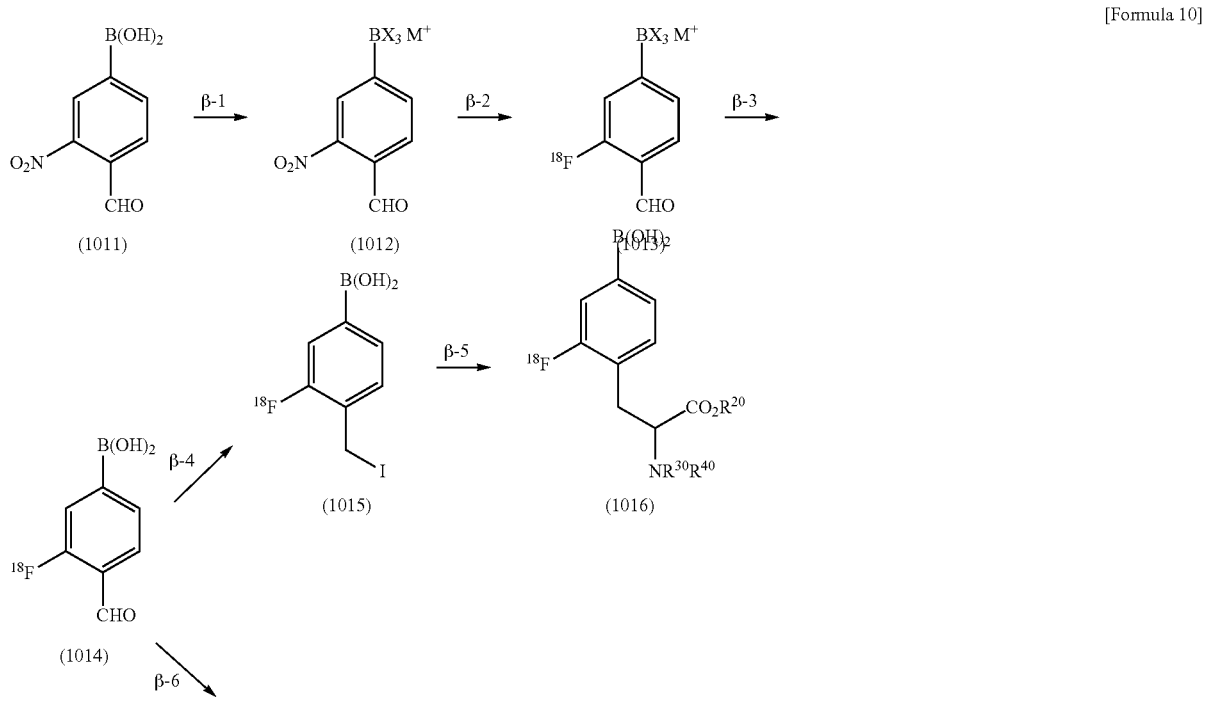
[Formula 10]

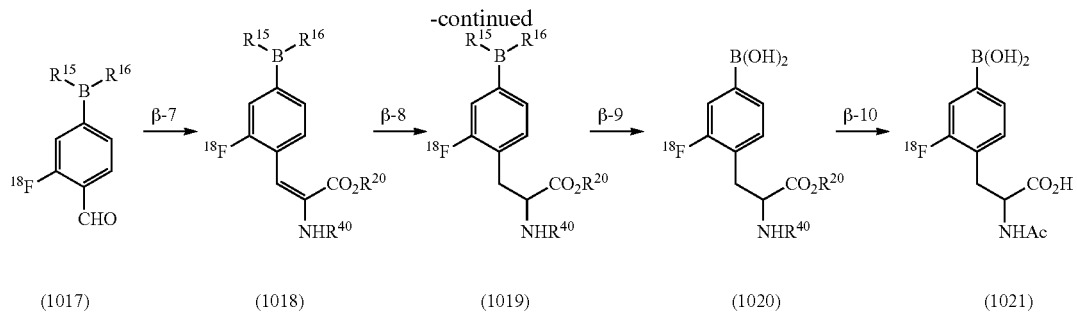

(1017)  (1018)  (1019)  (1020)  (1021)

Step γ

[Formula 11]

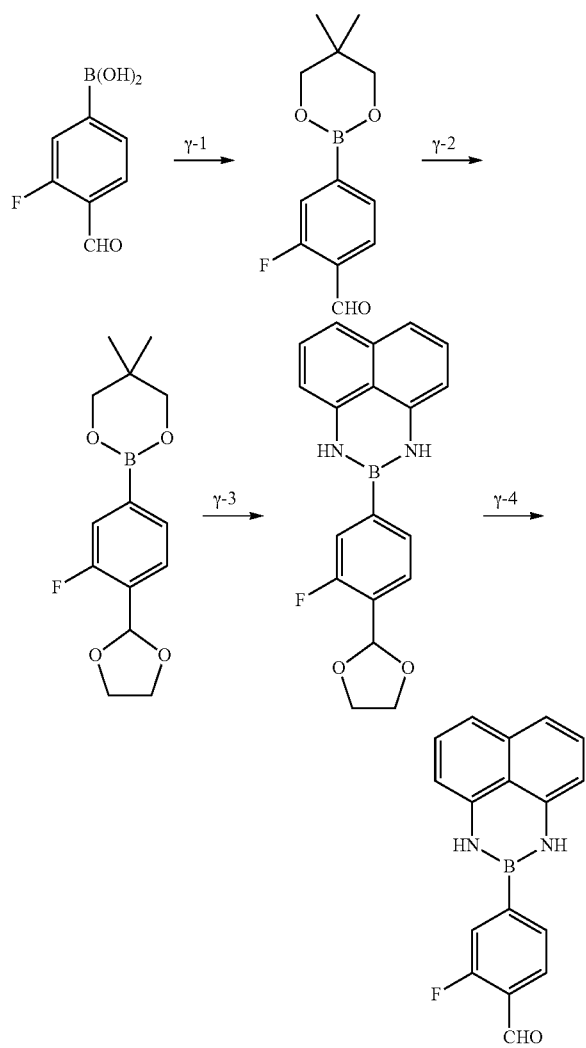

$R^{20}$ represents hydrogen or a protecting group $PG^1$ for a carboxylic acid. Here, $PG^1$ is not particularly limited and denotes any protecting group known by those skilled in the art for a carboxylic acid. Examples thereof include protecting groups described in Greene Wuts, "Protective Groups in Organic Synthesis", 3rd edition (a company, Wiley-Interscience in USA). Typically, the group concerned can be converted into an ester type to be protected, using ester condensation conditions or alkylation conditions. $PG^1$ is, for example, an alkyl group having 1 to 7 carbon atoms or an aromatic group such as a benzyl group. Specific examples thereof include alkyl groups such as methyl, ethyl, n-propyl, iso-propyl, n-butyl, iso-butyl, sec-butyl, tert-butyl, and n-pentyl groups, and aromatic groups such as a benzyl group and para-position-substituted benzyl groups such as p-methoxybenzyl and p-nitrobenzyl groups. Here, the para-position-substituted benzyl group denotes a benzyl group whose para-position is substituted with an alkyl group, an alkoxyl group, a nitro group, an amino group, or the like. $PG^1$ is in particular preferably a tert-butyl or benzyl group, which is not easily affected by racemization when the protected group is de-protected.

$R^{30}$ or $R^{40}$ independently represents hydrogen or a protecting group $PG^2$ for an amino group. The protecting group for an amino acid may be any protecting group known by those skilled in the art. Examples thereof include protecting groups described in Greene Wuts, "Protective Groups in Organic Synthesis", 3rd edition (the company, Wiley-Interscience in USA). Preferred examples thereof include benzyloxycarbonyl, acetyl, trifluroethylcarboxy, tert-butyloxycarbonyl, fluorenylmethyloxycarbonyl, trichloroethoxycarbonyl, trifluoroacetyl, allyloxycarbonyl, benzyl, propargyloxycarbonyl, benzoyl, phthaloyl, toluenesulfonyl, and nitrobenzenesulfonyl groups, although the protecting group is not limited thereto. Of these examples, benzyloxycarbonyl and tert-butyloxycarbonyl groups are preferred, which can be subjected to de-protection in a short period of time. Furthermore, $R^{30}$ or $R^{40}$ may be one that forms disubstituted methyleneamino together with N.

In the present specification, when $R^{15}$ and $R^{16}$ are combined together with B (boron atom) to form a ring as a protecting group for B, $R^{15}$ and $R^{16}$ are each preferably a group that forms a saturated or unsaturated 3- to 10-membered ring which may be substituted. Examples of the structure of the ring herein also include spiro-rings and condensed rings. Examples of the group that can form the ring include pinacol, 2,2-dimethyl-1,3-propanediol, N-methyldiethanolamine, 1,8-diaminonaphthalene, N-methyliminodiacetic acid, 1,1,1-trishydroxymethylethane, and catechol, although the group is not limited. In particular, pinacol is preferred.

In the reaction in each step of Step α and Step β, the reaction temperature varies in accordance with the solvent, the starting materials, the reagent(s), and others, and is appropriately selected. Also, the reaction period varies in accordance with the solvent, the starting materials, the reagent(s), the reaction temperature, and others, and is appropriately selected.

In the reaction in each of the steps, the target compound in each step may be isolated from the reaction mixture by a routine procedure after the end of each reaction.

The target compound is obtained, for example, by (i) filtrating away the catalyst and other insoluble substances in accordance with the needs, (ii) adding, to the reaction mixture, water and a solvent immiscible with water (for example, ethyl acetate, chloroform, or the like) to extract the target compound, (iii) washing the organic layer with water and using a drying agent such as anhydrous magnesium sulfate to dry the resultant in accordance with the needs, and (iv) distilling off the solvent. The obtained target compound may be further purified by a known method (for example, silica gel column chromatography or the like) in accordance with the needs. Also, the target compound in each of the steps may be supplied to the next reaction without purification.

In the present invention, it is important to synthesize first the $^{18}$F-labeled formyl-group-containing compound of the present invention temporarily. Once the $^{18}$F-labeled formyl-group-containing compound of the present invention can be prepared, an F-labeled BPA can be finally produced in the subsequent reaction by a method similar to the method of allowing reaction to proceed from an ordinary compound having F in accordance with the description of the present specification. In preparing the $^{18}$F-labeled formyl-group-containing compound of the present invention, for example, accelerated protons are radiated to $H_2^{18}O$ to synthesize $H^{18}F$-hydrofluoric acid through $^{18}O$ (p, n) reaction, and then this acid is passed through an ion exchange resin column to be adsorbed thereon to separate this acid from $H_2^{18}O$ which is a non-adsorbed starting material. This column is subjected to elution with an aqueous solution of $K_2CO_3$ to yield $K^+ \, ^{18}F^-$, which is preferably used as a nucleophilic agent.

(Step α)

Step α-1 is a step of subjecting the compound to $^{18}$F fluorination by using $^{18}$F$^-$. For example, $H^{18}F$ produced through $^{18}O$ (p, n) $^{18}$F reaction using protons generated from an accelerator and $H_2^{18}O$ is prepared into $K^{18}F$/Kryptofix (2,2,2) by a routine procedure. For example, a solution of $K^{18}F$/Kryptofix(2,2,2) in DMSO is added to 4-bromo-2-nitrobenzaldehyde, and the resultant is stirred under heat for a predetermined period of time.

After the end of the reaction, a diluting solution such as acetonitrile is added to the reaction mixture, so as to prepare a reaction confirmation solution.

The solvent to be used is not limited to DMSO, and examples thereof include acetonitrile, DMF, THF, dioxane, alcohol-based solvents such as ethanol and isopropanol, chloroform, dichloromethane, ethyl acetate, acetone, and mixed solvents each composed of two or more kinds of these solvents. Among these, DMSO and acetonitrile are preferred.

The reaction temperature is preferably from 100 to 200° C. or higher, more preferably from 120 to 180° C. The reaction period is preferably from 3 minutes to 2 hours, more preferably from 5 minutes to 1 hour.

(Step α-2)

In Step α-2,4-halogen-2-fluorobenzaldehyde is dissolved in methanol, and thereafter the resultant is caused to react with NaBH$_4$ at room temperature for several minutes to several hours. Thereafter, water is added thereto, and extraction is carried out using ethyl acetate or the like.

The reagent to be used is a reducing agent such as NaBH$_4$ or LiAlH$_4$.

The solvent to be used is not particularly limited, and examples thereof include, in addition to methanol, alcohol-based solvents such as ethanol, THF, dioxane, acetone, ethyl acetate, benzene, toluene, chloroform, and carbon tetrachloride, among which alcohol-based solvents such as methanol and ethanol are particularly preferred.

The reaction temperature is preferably from 0 to 120° C., more preferably from 0 to 40° C.

The reaction period is preferably from 1 hour to 24 hours, more preferably from 5 minutes to 1 hour.

Step α-3 is a step of producing 4-halogen-2-fluorobenzyl bromide. The compound obtained in α-2 is dissolved into hydrobromic acid, and the resultant is caused to undergo a reaction for several minutes.

The reacting agent to be used is not limited; however, in addition to hydrobromic acid, N-bromosuccinimide, thionyl chloride, and the like are preferably used. In view of reaction rate, hydrobromic acid is particularly preferred.

Preferred examples of the solvent to be used include dichloromethane, chloroform, carbon tetrachloride, ether-based solvents such as THF, and water. In particular, water is preferred in view of the environment.

The reaction temperature is preferably from −20° C. to 160° C., more preferably from room temperature to 120° C.

The reaction period is preferably from 5 minutes to 24 hours, more preferably from 5 to 15 minutes.

The obtained compound may be purified; however, the compound may be shifted to the next step without purification.

(Step α-4)

Step α-4 is a step of producing 4-halogen-2-fluorobenzyl iodide (production of compound 1005). The formyl group of the compound 1002 is iodinated. The iodinating reagent is not limited, and a known reagent such as 1,3-diiodo-5,5'-dimethylhydantoin, N-iodosuccinimide, or diiodosilane is used.

(Step α-5)

Step α-5 is a step of causing the compound 1004 or 1005 to react with a phase transfer catalyst and a modified amino acid that are generally used in Maruoka's reaction in the presence of a base to produce a compound 1006.

The modified amino acid to be used in Maruoka's reaction is not limited. Preferred examples thereof include a methyl ester of N-diphenylmethyleneglycine, an ethyl ester of N-diphenylmethyleneglycine, a t-butyl ester of N-diphenylmethyleneglycine N-diphenylmethyleneglycine, a t-butyl ester of 4-chlorobenzylideneglycine, and a benzyl ester of N-diphenylmethyleneglycine. Of these examples, particularly preferred is a t-butyl ester of N-diphenylmethyleneglycine.

The base to be used is not limited. Preferred examples thereof include lithium hydroxide, sodium hydroxide, potassium hydroxide, and triethylamine. In view of the reaction rate, potassium hydroxide is particularly preferred.

Preferred examples of the phase transfer catalyst to be used in Maruoka's reaction include O-allyl-N-(9-anthracenylmethyl)cinchonidinium bromide, and (S)-(+)-4,4-dibutyll-2,6-bis(3,4,5-trifluorophenyl)-4,5-dihydro-3H-dinaphtho[7,6,1,2-cde]azemipium bromide.

Preferred examples of the solvent to be used include toluene, dichloromethane, and chloroform. Toluene is particularly preferred in view of the environment.

The reaction temperature is preferably from −20° C. to 100° C., more preferably from −4° C. to room temperature.

The reaction period is preferably from 30 minutes to 24 hours, more preferably from 1 hour to 18 hours.

(Step α-6)

Step α-6 is a step of boronating the compound 1006. $R^{15}$ and $R^{16}$ can be combined together with B (boron atom) to form a ring as a protecting group for B. Examples of the structure of the ring herein also include spiro-rings and condensed rings. Examples of the group that can form the ring include pinacol, 2,2-dimethyl-1,3-propanediol, N-methyldiethanolamine, 1,8-diaminonaphthalene, N-methyliminodiacetic acid, 1,1,1-trishydroxymethylethane, and catechol, although the group is not limited. In particular, pinacol is preferred. In the case of producing a pinacol boronic acid derivative, a pinacol borylation reagent can be used in the presence of a palladium catalyst and a ligand. During this step, microwave radiation or the like can be used. Examples of the catalyst to be used include palladium catalysts used generally in Suzuki-Miyaura coupling reactions, such as a palladium chloride cinnamyl complex, palladium acetate, and trisdibenzylideneacetone dipalladium although the catalyst is not limited to these compounds.

The microwave radiation conditions are preferably from room temperature to 200° C., more preferably from 80° C. to 180. The reaction period is preferably from 1 minute to 60 minutes, more preferably from 5 minutes to 30 minutes.

Examples of the ligand include phosphorus-based ligands used generally in Suzuki-Miyaura coupling reactions, such as tricyclohexylphosphine,
2-dicyclohexylphosphino-2,4,6-triiso-propylbiphenyl,
2-dicyclohexylphosphino-2, —(N,N)-dimethylaminobiphenyl,
3,5-dimethoxy-2-dicyclohexylphosphino-2,4,6-triisopropylbiphenyl, and
3,5-dimethoxy-2-ditert-butylphosphino-2,4,6-triisopropylbiphenyl, although the ligand is not limited to these compounds.

Examples of the base to be used include lithium hydroxide, sodium hydroxide, potassium hydroxide, sodium carbonate, potassium carbonate, and triethylamine, although the base is not limited thereto. In particular, sodium carbonate and potassium carbonate are preferred, which are mild. Preferred examples of the solvent to be used include toluene, dioxane, and DMDO.

The compound obtained in the above-described manner may be de-protected by a routine procedure to obtain the target $^{18}$F-labeled BPA.

(Step β-1)

Step β-1 is a production step of trihalogenating the boronic acid part of the compound 1011. For example, an aqueous solution of potassium fluoride is added to a suspension of 4-formyl-3-fluorophenylboronic acid in acetonitrile, the system is stirred until the complete dissolution is attained, and then a solution of L-tartaric acid in THF is added. After the deposited precipitation is collected by filtration, the filtrate is concentrated under a reduced pressure.

Examples of the fluoride salt to be used include, in addition to potassium fluoride, sodium fluoride, lithium fluoride, and magnesium fluoride, although the fluoride salt is not limited. More preferably, potassium fluoride is used.

Examples of the reagent to be used include L-tartaric acid, citric acid, and acetic acid, although the reagent is not limited. More preferably, L-tartaric acid is used.

Examples of the solvent to be used include DMSO, DMF, water, dichloromethane, acetone, acetonitrile, THF, methanol, ethanol, and mixed solvents each composed of two or more kinds of these solvents. Of these examples, preferred is a combination of acetonitrile, water, and THF. The reaction temperature is preferably from 0 to 100° C., more preferably from 10 to 40° C.

(Step β-2)

Step β-2 is a reaction of labeling the compound 1012 with $^{18}$F in the presence of K$^{18}$F/Kryptofix(2,2,2). H$^{18}$F produced through $^{18}$O (p, n) $^{18}$F reaction using protons generated from an accelerator and H$_2$$^{18}$O is prepared into K$^{18}$F/Kryptofix (2,2,2) by a routine procedure. For example, a solution of K$^{18}$F/Kryptofix(2,2,2) in DMSO is added to a 4-formyl-3-fluorophenyltrifluoroborate potassium salt, and the resultant is stirred under heat for a predetermined period of time.

After the end of the reaction, a diluting solution such as acetonitrile is added to the reaction mixture, so as to prepare a reaction monitoring solution.

The solvent to be used is not limited to DMSO, and examples thereof include acetonitrile, DMF, THF, dioxane, alcohol-based solvents such as ethanol and isopropanol, chloroform, dichloromethane, ethyl acetate, acetone, and mixed solvents each composed of two or more kinds of these solvents. Among these, DMSO and acetonitrile are preferred.

The reaction temperature is preferably from 100 to 100° C. or higher, more preferably from 120 to 180° C. The reaction period is preferably from 3 minutes to 2 hours, more preferably from 5 minutes to 1 hour.

(Step β-3)

Step β-3 is a step of subjecting the compound (1013) to hydrolysis to produce a boronic acid. For example, after THF and water are added to a 4-formyl-3-fluorophenyltrifluoroborate potassium salt and iron(III) chloride and stirred, the filtrate obtained by filtration with neutral alumina is concentrated under a reduced pressure.

Examples of the reagent to be used include, in addition to iron(III) chloride, sodium hydroxide, potassium hydroxide, lithium hydroxide, aluminum oxide, silicon chloride, chlorotrimethylsilane, and silica gel, although the reagent is not limited thereto. Among these, iron(III) chloride is more preferable.

Examples of the solvent to be used include acetonitrile, DMSO, DMF, THF, water, methanol, ethanol, acetone, and mixed solvents each composed of two or more kinds of these solvents. Among these, a mixed solvent of THF and water is preferred.

The reaction temperature is preferably from −20° C. to 100° C., more preferably from 10 to 70° C. The reaction period is preferably from 5 minutes to 24 hours, more preferably from 10 minutes to 4 hours.

(Step β-4)

Step β-4 is a step of iodinating the formyl group of the compound 1014 to produce a compound 1015. The halogenating conditions are the same as those in α-3. The iodinating reagent is not limited, and a known reagent such as 1,3-diiodo-5,5'-dimethylhydantoin, N-iodosuccinimide, or diiodosilane is used.

(Step β-5)

Step β-5 is a step of causing the compound 1015 to react with a phase transfer catalyst and a modified amino acid that are generally used in Maruoka's reaction in the presence of a base to produce a compound 1016.

The modified amino acid to be used in Maruoka's reaction is not limited. Preferred examples thereof include a methyl ester of N-diphenylmethyleneglycine, an ethyl ester of N-diphenylmethyleneglycine, a t-butyl ester of N-diphenylmethyleneglycine N-diphenylmethyleneglycine, a t-butyl ester of 4-chlorobenzylideneglycine, and a benzyl ester of N-diphenylmethyleneglycine. Of these examples, particularly preferred is a t-butyl ester of N-diphenylmethyleneglycine.

The base to be used is not limited. Preferred examples thereof include lithium hydroxide, sodium hydroxide, potassium hydroxide, and triethylamine. In view of the reaction rate, potassium hydroxide is particularly preferred.

Preferred examples of the phase transfer catalyst to be used in Maruoka's reaction include O-allyl-N-(9-anthracenylmethyl)cinchonidinium bromide, and (S)-(+)-4,4-dibutyll-2,6-bis(3,4,5-trifluorophenyl)-4,5-dihydro-3H-dinaphtho[7,6,1,2-cde]azemipium bromide.

Preferred examples of the solvent to be used include toluene, dichloromethane, and chloroform. Toluene is particularly preferred in view of the environment.

The reaction temperature is preferably from −20° C. to 100° C., more preferably from −4° C. to room temperature.

The reaction period is preferably from 30 minutes to 24 hours, more preferably from 1 hour to 18 hours.

(Step β-6)

Step β-6 is a production step of esterifying the boronic acid part of the compound 1014 with 2,2-dimethyl-1,3-propanediol.

Examples of the solvent to be used include acetone, ethyl acetate, dichloromethane, chloroform, THF, dioxane, methanol, and ethanol. Among these, dichloromethane and THF are preferred, since these solvents are inactive to the reduction reaction.

The reaction temperature is preferably from −20° C. to 100° C., more preferably from room temperature to 50° C. The reaction period is preferably from 30 minutes to 24 hours, more preferably from 3 to 18 hours.

(Step β-7)

Step β-7 is a production step of turning the compound 1017 into an olefin by a Wittig-related reaction. The reaction agent to be used is not limited; however, a Wittig-related reaction or the like is preferably used. In view of the reaction rate, a Wittig-Horner reagent is particularly preferred.

The solvent to be used is an ether-based solvent such as THF, benzene, toluene, ethyl acetate, or the like. In particular, THF is preferred in view of ease in handling.

The reaction temperature is preferably from −100° C. to 0° C., more preferably from −80° C. to −200° C.

The reaction period is preferably from 5 minutes to 24 hours.

(Step β-8)

Step β-8 is a step of subjecting the compound 1018 to reduction hydrogenation to produce a compound 1019.

Examples of the catalyst to be used include palladium hydroxide and palladium carbon, although the catalyst is not limited thereto.

Examples of the solvent to be used include acetone, THF, methanol, and ethanol. Among these, methanol and ethanol are preferred, since these solvents are inactive to the reduction reaction.

The reaction temperature is preferably from −20° C. to 100° C., more preferably from room temperature to 50° C. The reaction period is preferably from 30 minutes to 24 hours, more preferably from 3 to 18 hours.

(Step β-9)

Step β-9 is a step of subjecting the compound 1019 to hydrolysis to eliminate 2,2-dimethyl-1,3-propanediol, so that a compound 1020 is produced.

As a reagent to be used in hydrolysis, an aqueous solution of sodium hydroxide or an aqueous solution of lithium hydroxide is used, although the reagent is not limited thereto.

The reaction temperature is preferably from −20° C. to 100° C., more preferably from room temperature to 50° C. The reaction period is preferably from 30 minutes to 24 hours, more preferably from 3 to 18 hours.

In the reaction of eliminating 2,2-dimethyl-1,3-propanediol, phenylboronic acid is used as a scavenger in a water-organic two-layer solvent system.

As the reaction solvent, dilute hydrochloric acid or dilute sulfuric acid can be used for the water layer, whereas diethyl ether, chloroform, or toluene can be used for the organic layer. Among these, dilute hydrochloric acid is preferable for the water layer, and diethyl ether is preferable for the organic layer.

The hydrolysis reaction temperature is preferably from −20° C. to 50° C., more preferably from room temperature to 40° C. The reaction period is preferably from 30 minutes to 24 hours, more preferably from 1 to 5 hours. Meanwhile, the reaction temperature for eliminating 2,2-dimethyl-1,3-propanediol is preferably from −20° C. to 50° C., more preferably from room temperature to 40° C. The reaction period is preferably from 30 minutes to 24 hours, more preferably from 1 to 18 hours.

(Step β-10)

Step β-10 is a step of de-protecting the compound 1020. For example, by optical resolution with use of aminoacylase, de-protection and optical resolution can be carried out simultaneously to produce a compound 1021.

The reaction temperature is preferably from room temperature to 50° C., more preferably from 30 to 40° C. The reaction period is preferably from 30 minutes to 48 hours, more preferably from 8 to 24 hours.

(Step γ-1)

Step γ-1 is a step of protecting formylphenylboronic acid as a boronic acid ester with use of a dihydric alcohol or the like. For example, this step can be carried out by dissolving formylphenylboronic acid and dimethylpropanediol into THF and causing the resultant to react.

Examples of the reagent to be used include pinacol, 2,2-dimethyl-1,3-propanediol, N-methylimonodiacetic acid, N-methyldiethanolamine, 1,8-diaminonaphthalene, 1,1,1-trishydroxymethylethane, and catechol, although the reagent is not limited thereto. More preferably, pinacol or 2,2-dimethyl-1,3-propanediol is used.

Examples of the solvent to be used include acetonitrile, DMSO, DMF, THF, water, methanol, ethanol, acetone, and mixed solvents each composed of two or more kinds of these solvents. Among these, THF is preferred.

The reaction temperature is preferably from −20° C. to 100° C., more preferably from 10° C. to 70° C. The reaction period is preferably from 5 minutes to 24 hours, more preferably from 10 minutes to 8 hours.

(Step γ-2)

Step γ-2 is a step of protecting the formyl group. For example, this step can be carried out by dissolving the compound obtained in γ-1 into a solvent such as benzene and subjecting the resultant to reflux reaction with addition of ethylene glycol and p-tosyl monohydrate.

Examples of the acid catalyst to be used include, in addition to paratoluenesulfonic acid, hydrochloric acid, sulfuric acid, and trifluoroacetic acid, although the acid catalyst is not limited thereto. More preferably, paratoluenesulfonic acid is used. Examples of the reagent to be used include dihydric alcohols such as ethylene glycol, pinacol, 1,3-propanediol, and 2,2-dimethylpropanediol; and monohydric alcohols such as methanol and ethanol, although not limited thereto. More preferably, ethylene glycol, which is a dihydric alcohol, is used.

Examples of the solvent to be used include DMSO, acetone, acetonitrile, THF, benzene, toluene, and xylene. Among these, benzene is preferred.

The reaction temperature is preferably from −20° C. to 120° C., more preferably from 20 to 100° C. The reaction period is preferably from 5 minutes to 24 hours, more preferably from 1 hour to 4 hours.

(Step γ-3)

Step γ-3 is a reaction of turning 5,5-dimethyl-1,3,2-dioxaborinane into a diaminonaphthalene derivative. For example, the reaction can be carried out by dissolving the compound obtained in γ-2 into tetrahydrofuran and adding diaminonaphthalene.

Examples of the solvent to be used include acetonitrile, DMSO, DMF, THF, acetone, toluene, xylene, and mixed solvents each composed of two or more kinds of these solvents. Among these, THF is preferred.

The reaction temperature is preferably from −20° C. to 120° C., more preferably from 10 to 70° C. The reaction period is preferably from 5 minutes to 24 hours, more preferably from 4 hours to 18 hours.

(Step γ-4)

Step γ-4 is a step of obtaining aldehyde by hydrolysis of acetal.

Examples of the solvent to be used include DMSO, THF, dioxane, water, methanol, ethanol, acetone, and mixed solvents each composed of two or more kinds of these solvents. Among these, THF is preferred.

The reaction temperature is preferably from −20° C. to 150° C., more preferably from 10 to 100° C. The reaction period is preferably from 5 minutes to 24 hours, more preferably from 10 minutes to 8 hours.

Once the $^{18}F$-labeled formyl-group-containing compound of the present invention is synthesized in each derivative, the subsequent synthesis can be allowed to proceed. When it is confirmed that the compound actually contains F and the synthesis proceeds, the same reaction can be carried out with a compound labeled with $^{18}F$ in place of F.

In the present invention, it is important to prepare first a $^{18}F$-labeled formyl-group-containing compound. Here, for example, accelerated protons are radiated to $H_2^{18}O$ to synthesize $H^{18}F$-hydrofluoric acid through $^{18}O$ (p, n) reaction, and then this acid is passed through an ion exchange resin column to be adsorbed thereon to separate this acid from $H_2^{18}O$, which is a non-adsorbed starting material. This column is subjected to elution with an aqueous solution of $K_2CO_3$ to yield $K^{+\,18}F^-$, which can be used as a nucleophilic agent to achieve fluorination with $^{18}F$.

[Formula 12]

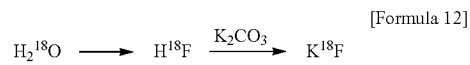

Furthermore, each protecting group can be de-protected by a routine procedure, whereby the target fluorinated BPA can be prepared.

The use of the method of the present invention makes it possible to yield such a $^{18}F$-labeled compound with a high yield in a state with excellent specific activity.

EXAMPLES

The present invention will be described in more detail byway of the following working examples; however, the invention is not limited to these examples.

In the examples below, the following machine and reagents were used for analyzing any compound and isolating/purifying the compound.

NMR spectra: (JNM-AL series AL400 manufactured by JEOL Ltd. at 400 MHz)

For microwave radiation, Initiator+ manufactured by Biotage Japan Ltd. was used.

Example 1

Production of [$^{18}F$]4-bromo-2-fluorobenzaldehyde $H^{18}F$ produced through $^{18}O$ (p, n) $^{18}F$ reaction using protons generated from an accelerator and $H_2^{18}O$ was prepared into $K^{18}F$/Kryptofix(2,2,2) by a routine procedure. A solution of $K^{18}F$/Kryptofix(2,2,2) (having a specific radioactivity of 36.8 MBq) in DMSO (1.0 mL) was added to 4-bromo-2-nitrobenzaldehyde (10 mg, 0.04 mmol), and the resultant was stirred at 120° C. for 10 minutes.

After the end of the reaction, acetonitrile (100 mL) was added to the reaction mixture for dilution, so as to prepare a reaction monitoring solution. The starting material 4-bromo-2-nitrobenzaldehyde, separately prepared [$^{19}F$]4-bromo-2-fluorobenzaldehyde, and the reaction monitoring solution were spotted on a silica gel plate and were developed by using a mobile phase (ethyl acetate/n-hexane=1/4).

The spot in the reaction monitoring solution attaining the same Rf value (Rf=0.7) as that of [$^{19}F$]4-bromo-2-fluorobenzaldehyde was confirmed by using a UV detector (wavelength of 254 nm) and a BAS system. Subsequently, the silica gel plate was cut and separated into fractions spot by spot, and the gamma-ray dose of each fraction was measured by using an automatic gamma counter. As a result, the radiochemical yield of [$^{18}F$] 4-bromo-2-fluorobenzaldehyde was 58%. FIG. 1 shows the result of thin layer chromatography at this time, where the left side shows detection by UV (254 nm), and the right view shows the fractions of the automatic gamma counter.

Example 2

Production of (4-bromo-2-fluorophenyl)methanol

Into methanol (50 mL) was dissolved 4-bromo-2-fluorobenzaldehyde (10.0 g, 48.8 mmol), and thereafter the resultant was caused to react with $NaBH_4$ (3.69 g, 97.6 mmol) at room temperature for 30 minutes. Thereafter, water (50 mL) was added thereto and, after extraction with ethyl acetate, the extraction layer was washed with water and a saturated saline solution, then dried over anhydrous magnesium sulfate, and concentrated under a reduced pressure to yield a compound (12.9 g, 99%).

The obtained compound was subjected to the next step without purification.

Example 3

Production of 4-bromo-2-fluorobenzyl bromide

The above compound (7.00 g, 34.1 mmol) was dissolved into 48% hydrobromic acid (35 mL), and the resultant was caused to react at 100° for 10 minutes. After the end of the reaction, the resultant was neutralized with potassium carbonate. Thereafter, extraction with ethyl acetate was carried out, and this extraction layer was washed with water and a saturated saline solution, then dried over anhydrous magnesium sulfate, and concentrated under a reduced pressure to yield a compound (8.35 g, 91%).

$^1H$-NMR ($CDCl_3$): 4.46 (s, 2H, BnC$\underline{H}_2$), 7.25-7.29 (m, 3H, Ar).

Example 4

Production of 4-iodo-2-fluorobenzyl iodide

First, diiodosilane (DIS) as a reaction agent was obtained by the following method. In other words, iodine (1.28 g) was caused to react with phenylsilane (2.50 mL) and ethyl acetate (0.15 mL) at room temperature. Thereafter, this reaction agent (DIS) was used directly in the subsequent reaction without purification.

Then, after 4-bromo-2-fluorobenzaldehyde (300 mg, 1.48 mmol) was dissolved into dichloromethane (50 mL), the whole amount of DIS prepared in advance was added thereto, and the resultant was caused to react at room temperature for 10 minutes. Thereafter, a 10% solution of sodium hydrogencarbonate (5 mL) and a 10% solution of sodium sulfite (5 mL) were added to separate an organic layer. This organic layer was washed with water and a saturated saline solution, then dried over anhydrous magnesium sulfate, and concentrated under a reduced pressure to yield a crude product 1004. This was further purified by silica gel column chromatography (n-hexane alone) to yield a target compound (423 mg, 91%).

$^1$H-NMR (CDCl$_3$): 4.58 (s, 2H, BnC$\underline{H}_2$), 7.23-7.32 (m, 3H, Ar).

Example 5

Production of tert-butyl 3-(4-bromo-2-fluorophenyl)-2-(diphenylmethyleneamino)-propanoate To toluene (100 mL) were added cesium hydroxide (7.54 g, 50.3 mmol), benzyl N-(diphenylmethylene)glycinate (5.50 g, 16.7 mmol), and O-ally-N-9-anthracenylmethylcinchonidiumbromide (1.10 g, 1.67 mmol, 0.1 equiv). The resultant was cooled to 0° C. Thereafter, while this toluene mixture solution was being violently stirred, a solution of the compound (4.47 g, 16.7 mmol) obtained in Example 3 in toluene (10 mL) is added all at a time. After the end of dropwise addition, the resultant was stirred for 30 minutes further. Thereafter, the reaction solution was washed with a saturated saline solution (50 mL) for three times, then dried over magnesium sulfate, and concentrated under a reduced pressure to yield a crude target compound (8.7 g). This was recrystallized with n-hexane to yield a target compound as a solid (2.68 g, 83%).

$^1$H-NMR (CDCl$_3$); 1.44 (s, 9H, t-Bu), 3.11 (dd, J=8.8, 13.2, 1H, CH$_2$-α), 3.26 (dd, J=4.4, 13.6, 1H, CH$_2$-β), 4.17 (dd, J=4.4, 9.2, 1H, CH), 6.73 (d, J=6.4, 2H, Ar), 7.01-7.13 (m, 3H, Ar), 7.29-7.40 (m, 6H, Ar), 7.57 (m, 2H, Ar).

Meanwhile, from the compound obtained in Example 4, a target compound (yield of 80%) was synthesized in a similar manner.

Example 6

Production of tert-butyl 2-(diphenylmethyleneamino)-3-(2-fluoro-4-(4,4,5,5-tetramethyl-1,3,2-dioxaborolane-2-yl)phenyl) propanoate Under a nitrogen gas flow, PdCl$_2$(dba) (27.5 mg, 0.03 eq.) and tricyclophosphine (16.8 mg, 0.06 eq.) were suspended into dioxane (5 ml), and this suspension was stirred for 30 minutes. Thereafter, bis(pinacolate)diborane (305 mg, 1.20 mmol) and KOAc (294 mg, 3.00 mmol) were added thereto, and further the above-mentioned compound (482 mg, 1.00 mmol) was added thereto.

Thereafter, microwave radiation was carried out at 150° C. for 15 minutes to yield a target compound (418 mg, 79%).

$^1$H-NMR (CDCl$_3$); 1.33 (s, 12H, pinacol), 1.44 (s, 9H, t-Bu), 3.17 (dd, J=9.6, 13.6, 1H, CH$_2$-α), 3.34 (dd, J=4.0, 13.6, 1H, CH$_2$-β), 4.20 (dd, J=4.0, 9.2, 1H, CH), 6.67 (d, J=6.0, 2H, Ar), 7.08-7.16 (m, 2H, Ar), 7.27-7.82 (m, 9H, Ar).

Example 7

Production of 4-formyl-3-fluorophenyltrifluoroborate Potassium Salt

Into acetonitrile (24 mL) was suspended 4-formyl-3-fluorophenylboronic acid (1.00 g, 5.95 mmol), and potassium fluoride (1.38 g, 23.8 mmol) dissolved in water (2.4 mL) was added thereto. The resultant was stirred until complete dissolution was attained.

Subsequently, L-tartaric acid (1.83 g, 12.2 mmol) was dissolved in THF, and the resultant was added into the reaction solution slowly in 10 minutes. The deposited colorless precipitation was separated by filtration and, after washing well with acetonitrile, the filtrate was collected. The collected filtrate was concentrated under a reduced pressure to yield a targeted 4-formyl-3-fluorophenyltrifluoroborate potassium salt as a colorless crystal (1.10 g, 80.2%).

$^1$HNMR (DMSO-D6): δ=7.11 (m, 1H), 7.29 (d, J=7.2 Hz, 1H), 7.59 (dd, J=7.2 Hz, 1H), 10.1 (s, 1H)

Example 8

Production of 4-formyl-3-[$^{18}$F]fluorotrifluoroborate Potassium Salt

H$^{18}$F produced through $^{18}$O (p, n) $^{18}$F reaction using protons generated from an accelerator and H$_2$$^{18}$O was prepared into K$^{18}$F/Kryptofix(2,2,2) by a routine procedure. A solution of K$^{18}$F/Kryptofix(2,2,2) (having a specific radioactivity of 23.0 MBq) DMSO (1.0 mL) was added to a 4-formyl-3-fluorophenyltrifluoroborate potassium salt (12.5 mg, 0.05 mmol), and the resultant was stirred at 120° C. for 10 minutes.

After the end of the reaction, acetonitrile (100 mL) was added to the reaction mixture for dilution, so as to prepare a reaction monitoring solution. The starting material 4-formyl-3-fluorophenyltrifluoroborate potassium salt and the reaction monitoring solution were spotted on a silica gel plate and were developed by using a mobile phase (chloroform/methanol=4/1).

Figure 2:
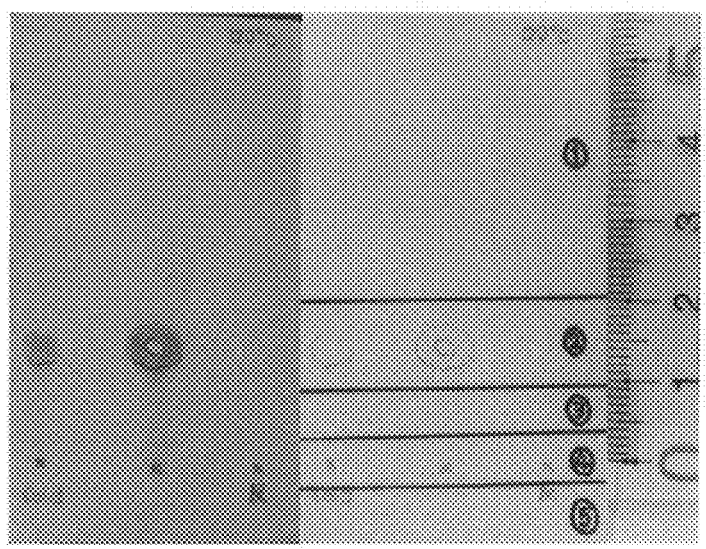
FIG. 2 shows a result of thin layer chromatography that confirms synthesis of a novel compound of the present invention.

The spots in the reaction monitoring solution were confirmed by using a UV detector (wavelength of 254 nm) and a BAS system. Subsequently, the silica gel plate was cut and separated into fractions spot by spot, and the gamma-ray dose of each fraction was measured by using an automatic gamma counter. As a result, the radiochemical yield of 4-formyl-3-[$^{18}$F]fluorophenyltrifluoroborate potassium salt was 12.3%. FIG. 2 shows the result of thin layer chromatography at this time, where the left side shows detection by UV (254 nm), and the right view shows the fractions of the automatic gamma counter.

Example 9

Production of 4-formyl-3-fluorophenylboronic acid

To a 4-formyl-3-fluorophenyltrifluoroborate potassium salt (100 mg, 0.44 mmol) and iron(III) chloride (77 mg, 0.48 mmol) were added THF (1 mL) and water (1 mL), respectively, and the resultant was stirred for 10 minutes. The reaction solution was filtrated with neutral alumina, and the filtrate was concentrated under a reduced pressure to yield a targeted 4-formyl-3-fluorophenylboronic acid as a colorless crystal (60 mg, 82%).

1HNMR (DMSO-D6): δ=7.60-7.80 (m, 3H), 8.60 (br, 2H), 10.2 (s, 1H)

Example 10

4-(3-tert-butoxy-2-(diphenylmethyleneamino)-3-oxopropyl)-3-[18]fluorophenylboronic acid The formyl group of the compound obtained in Example 9 is iodinated. First, diiodosilane (DIS) as a reaction agent is obtained. Iodine is caused to react with phenylsilane and ethyl acetate at room temperature. Thereafter, this reaction agent (DIS) can be used directly in the subsequent reaction without purification.

Subsequently, after the compound obtained in Example 9 is dissolved into dichloromethane, the whole amount of DIS prepared in advance is added thereto, and the resultant is caused to undergo a reaction at room temperature for 10 minutes. Thereafter, a 10% solution of sodium hydrogencarbonate and a 10% solution of sodium sulfite solution are added to separate an organic layer. This organic layer is washed with water and a saturated saline solution, then dried over anhydrous magnesium sulfate, and concentrated under a reduced pressure to yield a crude product.

The obtained crude product, (diphenylmethylene)glycine tertbutyl ester, O-allyl-N-9-anthracenylmethylcinchonidium bromide, and cesium hydroxide monohydrate (163.9 mg) are suspended in dichloromethane (5 mL). Thereafter, the resultant is stirred for 10 minutes. After the catalyst is filtered out, the filtrate is concentrated under a reduced pressure to yield a target crude product.

To the crude product obtained in the above reaction is added trifluoroacetic acid or a hydrogen chloride acid-containing ethyl acetate solution, and the resultant is caused to undergo a reaction at room temperature for 5 minutes. The reaction mixture is concentrated under a reduced pressure and purified by semi-preparative HPLC to yield a target compound.

Example 11

4-(5,5-dimethyl-[1,3,2]dioxaborinane-2-yl)-2-fluorobenzaldehyde 3-fluoro-4-formyl-phenylboronic acid (5.07 g, 30.3 mmol), 2,2-dimethyl-1,3-propanediol (3.83 g, 36.8 mmol), and anhydrous tetrahydrofuran (40 ml) were put and stirred for 5 hours. After the disappearance of the starting material was confirmed by TLC, the solvent was distilled off under a reduced pressure, and the residue was subjected to extraction with ether. The organic layer was washed with water and a saturated saline solution and, after drying (sodium sulfate), the solvent was concentrated under a reduced pressure to yield a target compound (6.64 g, 930).

1H-NMR (CDCl$_3$) 1.03 (6H, s, 2CH$_3$), 3.79 (4H, s, 2CH$_2$), 7.50-7.88 (3H, m, ArH), 10.39 (1H, s, CHO)

Example 12

2-benzyloxycarbonylamino-3-[4-(5,5-dimethyl-[1,3,2]dioxaborinane-2-yl)-2-fluorophenyl]acrylic acid methyl ester The compound obtained in Example 11 (3.96 g, 12.0 mmol) was dissolved into anhydrous tetrahydrofuran (80 ml), and the resultant was cooled to −78° C. with dry ice/acetone. After sufficient cooling, 1,1,3,3-tetramethylguanidine (1.5 ml, 28.7 mmol) was dropwise added thereto. After stirring for 5 minutes, a solution of the above compound (2.36 g, 10.0 mmol) in anhydrous tetrahydrofuran (20 ml) was dropwise added slowly. The temperature was raised back to room temperature overnight, and the resultant was further stirred for 24 hours. After the disappearance of the starting material was confirmed by TLC, the solvent was removed under a reduced pressure, and the residue was subjected to extraction with chloroform. The organic layer was washed with a phosphoric acid buffer solution (pH 7.0), then with a saturated saline solution and, after drying over sodium sulfate, the solvent was distilled off under a reduced pressure to yield a yellow oily product. This was purified by silica gel column chromatography (n-hexane:ethyl acetate=4:1) to yield a target compound (5.6 g, 84%).

1H-NMR (CDCl$_3$): 1.02 (6H, s, 2CH$_3$), 3.76 (4H, s, 2BOCH$_2$), 3.82 (3H, s, COOCH$_3$), 5.07 (2H, s, ArCH$_2$), 6.57 (1H, br, NH), 7.29-7.51 (9H, m, ArH, C=CH)

Example 13

2-acetylamino-3-[4-(5,5-dimethyl-[1,3,2]dioxaborinane-2-yl)-2-fluorophenyl]propanoic acid methyl ester In a reaction vessel for middle-pressure hydrogenation, the target compound (3.0 g, 6.8 mmol) was dissolved into methanol (30 ml), and 10% Pd—C (148 mg) and acetic anhydride (1.2 ml, 12.7 mmol) were added thereto. The resultant was stirred overnight under a hydrogen gas stream (3 atm). After the disappearance of the starting material was confirmed by TLC, the palladium catalyst was filtered off, and the filtrate was concentrated under a reduced pressure to yield a target compound (2.30 g, 96%).

1H-NMR (CDCl$_3$): 1.02 (6H, s, 2CH$_3$), 1.96 (3H, s, COCH$_3$), 3.14 (1H, dd, J=13.8, 5.6 Hz, ArCHH), 3.22 (1H, dd, J=13.8, 5.6 Hz, ArCHH), 3.73 (3H, s, COOCH$_3$), 3.76 (4H, s, 2BOCH$_2$), 4.85 (1H, dd, J=13.8, 5.6 Hz, NCH), 6.00 (1H, br, NH), 7.07-7.50 (3H, m, 3ArH)

Example 14

D,L-N-acetyl-4-borono-2-fluorophenylalanine

The target compound (2.02 g, 5.75 mmol) and water (50 ml) were put, and 1N NaOH (12 ml) was added thereto. The resultant was stirred for 3 hours. After the disappearance of the starting material was confirmed by TLC, 1N HCl (15 ml) was added thereto, and the resultant was stirred for 17 hours. Phenylboronic acid (0.610 g, 5 mmol) was dissolved into diethyl ether (3 ml), and this was added to the reaction mixture. The resultant was stirred for 3 hours. The deposited crystal was collected by filtration to yield a target compound (1.33 g, 86%).

1H-NMR (DMSO); 1.75 (3H, s, COCH3), 2.82 (1H, dd, J=13.8, 5.6, ArCHH), 3.11 (1H, dd, J=13.8, 5.6, ArCHH), 4.44 (1H, dd, J=14.2, 8.4, NCH), 7.20-7.52 (3H, m, 3ArH), 8.13 (2H, s, B(OH)2), 8.21 (1H, br, NH), 12.7 (1H, s, CO2H)

Example 15

L-4-borono-2-fluorophenylalanine

The target compound (500 mg, 1.86 mmol) and water (50 ml) were added, and a 1N aqueous solution of sodium hydroxide was added little by little to adjust pH to 7.8 (pH meter). D-aminoacylase (50 mg) was added thereto and, after the enzyme was dissolved, the resultant was stirred at 37° C. for 24 hours. After the reaction was confirmed by TLC, the enzyme was deactivated by stirring at 70° C. for 1 hour. The enzyme was filtered off with an ultrafilter, and the filtrate was passed through a column filled with a cation exchange resin (IR120, H$^+$). The solution that had passed through the ion exchange resin column was concentrated under a reduced pressure to yield a crude product of L-N-acetyl-4-borono-2-fluorophenylalanine (227.9 mg).

Further, water (23 ml) was added thereto, and 1N NaOH was added little by little to adjust pH to 7.8. L-aminoacylase (23 mg) was added thereto, and the resultant was stirred at 37° C. for 24 hours. After the reaction was confirmed by TLC, the enzyme was deactivated by stirring at 70° C. for 1 hour. The reaction mixture was passed through a column filled with a cation exchange resin (IR120, H$^+$). This column was subjected to elution with dilute ammonia water, and a fraction containing the target compound was concentrated under a reduced pressure to yield a target compound (141.2 mg, 73%) with an optical purity of 98.1% ee (HPLC).

$^1$H-NMR (DMSO); 3.15 (2H, m, ArC$\underline{H}_2$), 4.05 (1H, br, NC$\underline{H}$), 7.28-7.57 (3H, m, 3Ar$\underline{H}$), 8.22 (2H, s, B{O$\underline{H}$}$_2$), 8.51 (2H, br, N$\underline{H}_2$) [α]$_D$ 5.94 (c=1.005, HCl)

Example 16

Production of 4-(5,5-dimethyl-1,3,2-dioxaborinane-2-yl)-2-fluorobenzaldehyde (Step γ-1)

Into THF (50 mL) were dissolved 3-fluoro-4-formylphenylboronic acid (5.07 g, 30.3 mmol) and 2,2-dimethylpropanediol (3.83 g, 36.8 mmol), and the resultant was stirred at room temperature for 5 hours. After the solvent was concentrated under a reduced pressure, the residue was dissolved in ethyl acetate (50 mL), washed with water (50 mL) and further with a saturated saline solution (50 mL), and dried over MgSO$_4$. After MgSO$_4$ was filtered, the organic layer was concentrated to yield a target compound as a colorless oil (6.64 g, 93%).

$^1$H-NMR (CDCl$_3$); 1.03 (s, 6H, 2CH$_3$), 3.79 (s, 4H, 2CH$_2$), 7.50-7.88 (m, 3H, ArH), 10.39 (s, 1H, CHO).

Production of 2-(4-(1,3-dioxolane-2-yl)-3-fluorophenyl)-5,5-dimethyl-1,3,2-dioxaborinate (Step γ-2)

The compound obtained in Step γ-1 (1.18 g, 5.00 mmol) was dissolved into benzene (20 mL), and ethylene glycol (1.24 g, 20.0 mmol) and p-tosylic acid monohydrate (38 mg, 0.20 mmol) were added thereto. The resultant was subjected to reflux reaction while removing water for 3 hours. After the end of the reaction, the resultant was cooled to room temperature. The reaction solvent was washed with a 0.1 N aqueous solution of sodium hydroxide for 3 times and with a saturated saline solution for one time, followed by adding MgSO$_4$ for drying. This was filtered, then concentrated under a reduced pressure, and purified with a silica gel column (hexane:ethyl acetate=20:1) to yield a target compound as a white crystal (700 mg, 50%).

$^1$H-NMR (CDCl$_3$); 1.01 (s, 6H, 2CH$_3$), 3.69-3.78 (m, 8H, 4CH$_2$), 5.70 (s, 1H, CHO), 7.26-7.70 (m, 3H, ArH).

2-(4-(1,3-dioxolane-2-yl)-3-fluorophenyl)-2,3-dihydro-1H-naphtho[1,8-de]-1,3,2-diazaborinine (Step γ-3)

The compound obtained in Step γ-2 (280 mg, 1.00 mmol) was dissolved into tetrahydrofuran (10 mL), and diaminonaphthalene (158 mg, 1.00 mmol) was added thereto. The resultant was caused to undergo a reaction at room temperature for 18 hours. The solvent was concentrated under a reduced pressure and purified with a silica gel column (hexane:ethyl acetate=20:1) to yield a target compound as a red crystal (100 mg, 30%).

$^1$H-NMR (CDCl$_3$); 3.36-3.80 (m, 4H, 2CH$_2$), 5.70 (d, 1H, ArCHO), 5.93 (s, 2H, 2NH), 6.40-7.76 (m, 9H, ArH).

2-fluoro-4-(1H-naphtho[1,8-de]-1,3,2-diazaborinine-2(3H)-yl)benzaldehyde (Step γ-4)

Hydrolysis of acetal by a routine procedure yielded aldehyde (78%).

What is claimed is:
1. A compound of the following formula below:

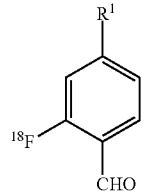

wherein R$^1$ represents a bromo group, an iodo group, a diazaborinane derivative, BX$_3^-$ or BX$_3^-$M$^+$ (wherein X represents a halogen, and M$^+$ represents a monovalent monoatomic cation, a polyatomic cation, or a complex cation).

2. The compound according to claim 1, wherein X represents F, and M$^+$ represents an alkali metal ion, an ammonium ion, a tetraalkylammonium ion, a tetraarylammonium ion, a tetraalkylphosphonium ion, a tetraarylphosphonium ion, or an imidazolium ion.

3. A method for producing $^{18}$F-labeled 4-boronophenylalanine (BPA), comprising:
producing a brominated compound of the following formula (a) by reacting the compound of claim 1 with a brominating reagent, or producing a iodinated compound of the following formula (b) by reacting the compound of claim 1 with a iodinating reagent;

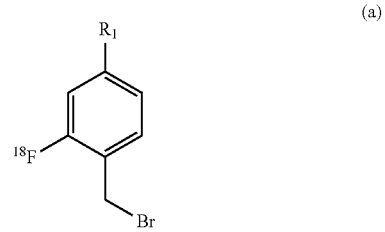

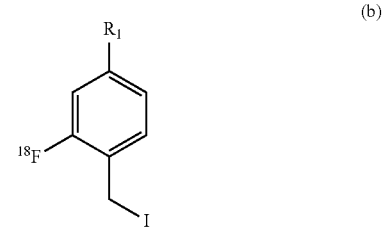

producing a compound of the following formula (c) by reacting the brominated compound of formula (a) or the iodinated compound of formula (b) with a phase transfer catalyst and a protected amino acid; and

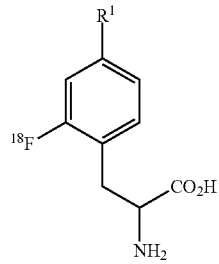

(c)

producing the $^{18}$F-labeled 4-boronophenylalanine (BPA) compound of the following formula (d) by boronating the compound of formula (c);

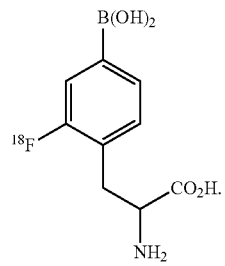

(d)

4. The method for producing $^{18}$F-labeled BPA according to claim 3, wherein X represents F, and M$^+$ represents an alkali metal ion, an ammonium ion, a tetraalkylammonium ion, a tetraarylammonium ion, a tetraalkylphosphonium ion, a tetraarylphosphonium ion, or an imidazolium ion.

* * * * *